United States Patent
Jojic et al.

(10) Patent No.: US 7,840,358 B2
(45) Date of Patent: Nov. 23, 2010

(54) HIERARCHICAL STATISTICAL FRAMEWORK FOR SEPARATING MIXED DATA

(75) Inventors: Nebojsa Jojic, Redmond, WA (US); Delbert Dwayne Dueck, Toronto (CA)

(73) Assignee: Microsoft Corporation, Redmond, WA (US)

( * ) Notice: Subject to any disclaimer, the term of this patent is extended or adjusted under 35 U.S.C. 154(b) by 1188 days.

(21) Appl. No.: 11/394,542

(22) Filed: Mar. 31, 2006

(65) Prior Publication Data

US 2007/0233392 A1 Oct. 4, 2007

(51) Int. Cl.
*G06F 19/00* (2006.01)
(52) U.S. Cl. .......................................... 702/20; 702/19
(58) Field of Classification Search .................. None
See application file for complete search history.

(56) References Cited

OTHER PUBLICATIONS

Marth et al. (Nature Genetics (1999) vol. 23, pp. 452-456).*
Ewing and Green (Genome Research (1998) vol. 8, pp. 186-194).*
Andrade and Manolakos (Journal of VLSI Signal Processing (2003), vol. 35, pp. 229-243).*
B. Ewing, et al., Base-Calling of Automated Sequencer Traces Using Phred. I. Accuracy Assessment, Genome Research, 1998, vol. 8, pp. 175-185.
N. Haan, et al., Bayesian Models for DNA Sequencing. Proceedings of IEEE Conference on Acoustics, Speech, and Signal Processing, 2002, vol. IV, pp. 4020-4023.
M. Jordan, et al., An Introduction to Variational Methods for Graphical Models, in M.I. Jordan (ed.), Learning in Graphical Models, 1998, Norwell, MA: Kluwer Academic Publishers.
C. Moore, et al., Evidence of HIV-1 Adaptation to HLA-Restricted Immune Responses at a Population Level. Science, 2002, vol. 296, pp. 1439-1443.
J. Prober, et al., A System for Rapid DNA Sequencing with Fluorescent Chain-Terminating Dideoxynucleotides. Science, Oct. 16, 1987, vol. 238, pp. 336-341.
F. Sanger, et al., DNA Sequencing with Chain-Terminating Inhibitors. Proceedings of the National Academy of Sciences of the United States of America (PNAS), Dec. 1, 1977, vol. 74, No. 12, pp. 5463-5467.
H. Swerdlow, et al., Capillary Gel Electrophoresis for Rapid, High Resolution DNA Sequencing. Nucleic Acids Research, Feb. 20, 1990, vol. 18, No. 6, pp. 1415-1419.

* cited by examiner

*Primary Examiner*—Lori A Clow
(74) *Attorney, Agent, or Firm*—Lee & Hayes, PLLC

(57) ABSTRACT

A hierarchical statistical framework for separating mixed data is provided. The approach is a shift from chaining hard-decision modules to an integrated soft-decision approach. The framework facilitates separating, for instance, sequencing data obtained from a mixture of two or more different sequences. The sequencing data can be separated using machine learning techniques to determine the correspondence between the sequencing data and the two or more different sequences.

20 Claims, 15 Drawing Sheets

Raw data:

Processed data:

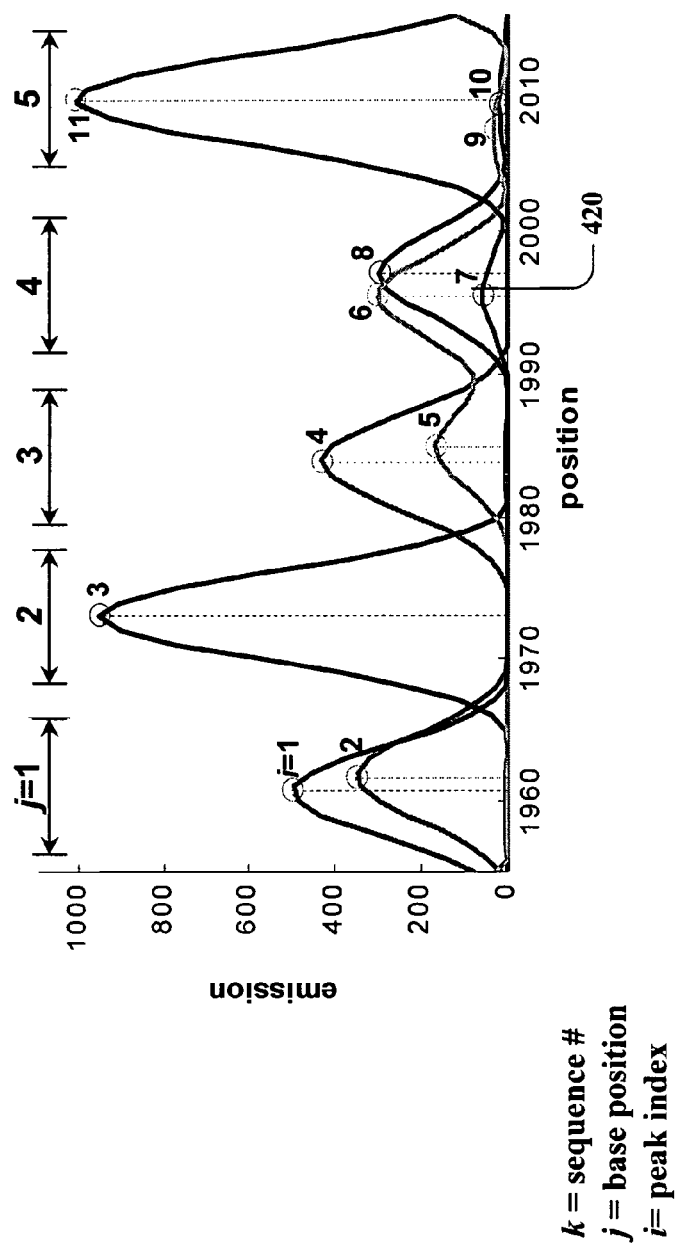
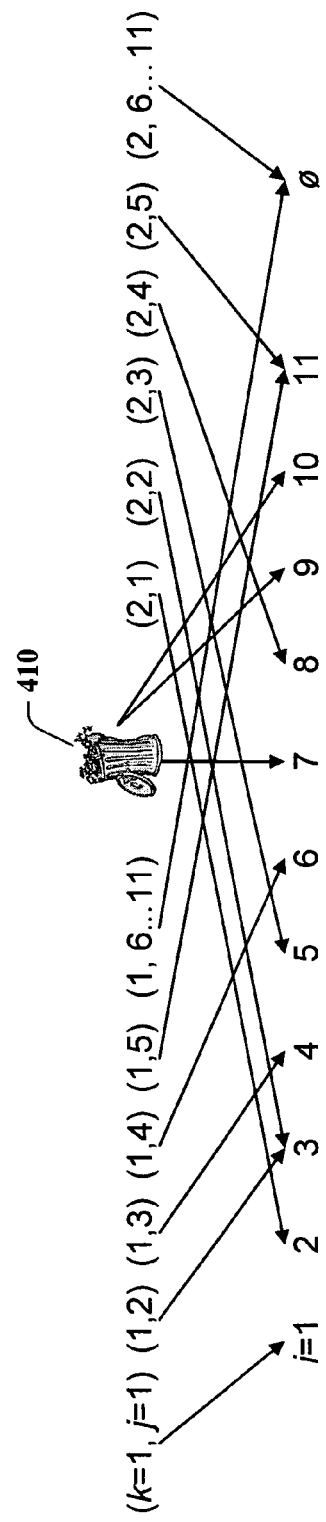
$k$ = sequence #
$j$ = base position
$i$ = peak index
FIG. 4

FIG. 5A

$$R^1 = \begin{bmatrix} 1 & 0 & 0 & 0 & 0 & 0 & 0 & 0 & 0 & 0 \\ 0 & 0 & 1 & 0 & 0 & 0 & 0 & 0 & 0 & 0 \\ 0 & 0 & 0 & 1 & 0 & 0 & 0 & 0 & 0 & 0 \\ 0 & 0 & 0 & 0 & 0 & 1 & 0 & 0 & 0 & 0 \\ 0 & 0 & 0 & 0 & 0 & 0 & 0 & 0 & 0 & 1 \end{bmatrix} \underbrace{\phantom{xxxxxxxxxxxxxxxxxxxxxx}}_{\text{Strain \#1} \quad 530}$$

510

$$R^2 = \begin{bmatrix} 0 & 1 & 0 & 0 & 0 & 0 & 0 & 0 & 0 & 0 \\ 0 & 0 & 0 & 1 & 0 & 0 & 0 & 0 & 0 & 0 \\ 0 & 0 & 0 & 0 & 1 & 0 & 0 & 0 & 0 & 0 \\ 0 & 0 & 0 & 0 & 0 & 0 & 1 & 0 & 0 & 0 \\ 0 & 0 & 0 & 0 & 0 & 0 & 0 & 0 & 0 & 1 \end{bmatrix} \underbrace{\phantom{xxxxxxxxxxxxxxxxxxxxxx}}_{\text{Strain \#2} \quad 540}$$

$$H^1 = R^1 X = \begin{bmatrix} 1 & 0 & 0 & 0 & 0 & 0 & 0 & 0 & 0 & 0 \\ 0 & 0 & 1 & 0 & 0 & 0 & 0 & 0 & 0 & 0 \\ 0 & 0 & 0 & 1 & 0 & 0 & 0 & 0 & 0 & 0 \\ 0 & 0 & 0 & 0 & 0 & 1 & 0 & 0 & 0 & 0 \\ 0 & 0 & 0 & 0 & 0 & 0 & 0 & 0 & 0 & 1 \end{bmatrix} \cdot \begin{bmatrix} 1960.7 \\ 1961.7 \\ 1973 \\ 1983.9 \\ 1984.9 \\ 1995.4 \\ 1995.6 \\ 1997 \\ 2007.1 \\ 2008.9 \\ 2009.3 \end{bmatrix} = \begin{bmatrix} 1960.7 \\ 1973 \\ 1983.9 \\ 1995.4 \\ 2009.3 \end{bmatrix}$$

510        550        560

HIERARCHICAL STATISTICAL FRAMEWORK FOR SEPARATING MIXED DATA

BACKGROUND

The biochemical processes used to build and maintain living organisms are controlled by chains of nucleic acids, such as deoxyribonucleic acid (DNA) and ribonucleic acid (RNA). Each nucleic acid is made up of a sequence of nucleotides consisting of a sugar (e.g., deoxyribose, ribose) and a nitrogen base having a triphosphate group (abbreviated as dNTP, d=deoxyribose, N=nitrogen base, TP=triphosphate). The bases that make up DNA are adenine (A), cytosine (C), guanine (G) and thymine (T). RNA molecules have the base uracil (U) instead of thymine.

A molecule of DNA can exist as two nucleic acid strands linked together by hydrogen bonds between the bases of each strand to form a double-helical structure (double-stranded DNA (dsDNA)). The bases will only bind specifically to each other (adenine to guanine and cytosine to thymine) such that the strands of a dsDNA molecule are complementary. DNA also can exist as a single-stranded molecule (ssDNA), such as the DNA in the parvovirus. A molecule of RNA can be single stranded (ssRNA), or in some organisms (e.g., rotavirus) it is double-stranded (dsRNA), with cytosine binding to uracil.

Determining the sequence of a nucleic acid strand is useful for a variety of research and commercial applications (e.g., basic science research, applied research, forensics, paternity testing, etc.). Thus, nucleic acid sequencing tools are some of the most important tools in biotechnology. One such exemplary useful tool is an automated fluorescent sequencer that sequences DNA by analyzing color signals emitted by fluorescently-labeled DNA fragments. Using the Sanger chain termination method, the DNA fragments are labeled with synthetic fluorescent nucleotides. Fluorescent nucleotides having different bases (A, C, G and T) are labeled with different fluorescent compounds so that each base emits a different color of light. The labeled fragments are then sorted by mass using polyacrylamide gel electrophoresis and the fluorescent signals emanating from the gel are detected. A software program (referred to as a base caller) identifies the base at a particular position in the sequence based on the color and intensity of the emissions.

Fluorescently labeled DNA fragments are produced using a polymerase chain reaction (PCR) performed with fluorescent dideoxynucleotides (ddNTPs: ddATP, ddCTP, ddGTP and ddTTP). PCR is a two-step technique for copying (amplifying) DNA. In this technique, a dsDNA sequence under study is denatured to separate the sides of the double-stranded DNA and incubated with DNA primers (synthesized DNA fragments), the four deoxyribonucleotide triphosphates (dNTPs: dATP, dCTP, dGTP and dTTP) and the polymerase enzyme. Since the primers will bind to a complementary sequence of DNA, the sequence of the primers is chosen to select for the particular sequence of DNA under study. The polymerase enzyme will extend the bound primers into complementary strands of the DNA under study using the dNTPs as substrates.

When enough of the target DNA fragment has been amplified through PCR, a final annealing is performed using the four fluorescent ddNTPs. The four fluorescent ddNTPs are labeled with different fluorescent compounds and so emit an identifying color. Since the ddNTPs do not have a hydroxyl group (—OH) on their sugar component to allow the next nucleotide to attach, the growing chain terminates. Because the length of the fragment depends on how soon the polymerase incorporated a ddNTP into the growing complementary strand (and blocked further growth of the strand), the resulting mixture contains DNA fragments of different lengths.

Polyacrylamide gel electrophoresis is used to sort the fragments by mass (i.e., length). To accomplish this, the mixture of fragments is placed in gel-filled capillaries and a voltage is applied across the capillaries to get the slightly-negative DNA moving downward. After the fragments have sufficiently migrated through the gel, a laser is used to scan the gel in a particular order to excite the fluorescent molecules. A detector then detects the emissions and the raw data is corrected for known issues with the method (e.g., non-linear gel mobility effect) to produce a chromatogram.

A base caller algorithm determines the sequence by analyzing the color, intensity and time (which corresponds to position) of the emissions. A schematic example of a chromatogram (traces) is shown in FIG. 1 and examples of raw traces and a processed chromatogram are shown in FIG. 2. In FIG. 1, different colors are represented by different types of lines (solid, broken and thickness), the y-axis indicates the intensity of the emission and the x-axis indicates the position of the base in the sequence.

The algorithms employed by base callers are imperfect. For instance, a base caller will assign the base to a sequence position by determining the emission with the largest amplitude at a given position (the peak). However, sampling errors due to the low sampling rate used to obtain the data can occur, leading the base caller to rely on a data point that is not a true peak (as shown in FIG. 3). In FIG. 3, an "x" represents a sampled data point and circles represent the data point chosen by the base caller to call the base.

Moreover, the base caller algorithm assumes that the sample being sequenced contains only a single version of the nucleic acid of interest. However, if the nucleic acid sample under study is, for instance, a DNA sequence taken from a population of organisms having polymorphic sequences (i.e., a genetic locus that varies in content across a population of organisms), the sample likely will contain multiple variants of the gene. Chromatograms of such mixed samples will show complex patterns reflecting combinations of alleles. This reduces the accuracy of the sequencing, often leading to the data being thrown out and the experiment repeated. Thus, existing base callers function best when a sample contains only a single sequence of DNA.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The subject matter described herein provides a hierarchical statistical framework for separating mixed data. By way of example, machine learning can be used to decipher mixed chromatograms obtained from a sample containing two or more different sequences. Suitable machine learning techniques include but are not limited to statistical inference, expectation maximization (EM), variational expectation maximization (VEM), variational decoupling, iterative learning, temporal smoothing and clever indexing, for example. The peaks of the mixed chromatogram can be mapped to each sequence present in the sample by modeling various features of the data (e.g., peak phase shift, peak amplitude and the nucleotide content of the sequences) using parametric functions and then estimating the parameters from the data. Machine learning techniques also can be used to process the data prior to decoding it. For instance, to determine the position of the peak amplitudes, machine learning techniques can be used to fit Gaussian peaks to the data or template peak shapes can be machine-learned from the raw data underlying the mixed chromatogram.

The following description and the annexed drawings set forth in detail certain illustrative aspects of the subject matter. These aspects are indicative, however, of but a few of the various ways in which the subject matter can be employed and the claimed subject matter is intended to include all such aspects and their equivalents. For ease of description, nucleotide sequences from HIV have been selected to illustrate how the subject matter can be employed. However, the subject matter is not limited to HIV nucleotide sequences.

BRIEF DESCRIPTION OF THE DRAWINGS

FIG. 4 schematically illustrates a mapping component.

FIG. 5A illustrates exemplary transformation matrices $R^1$ and $R^2$.

FIG. 5B illustrates the transformation matrix $R^1$ multiplied by a complete set of sequence positions X to yield the set of base positions corresponding to the first sequence $H^1$.

DETAILED DESCRIPTION

Figure 1:
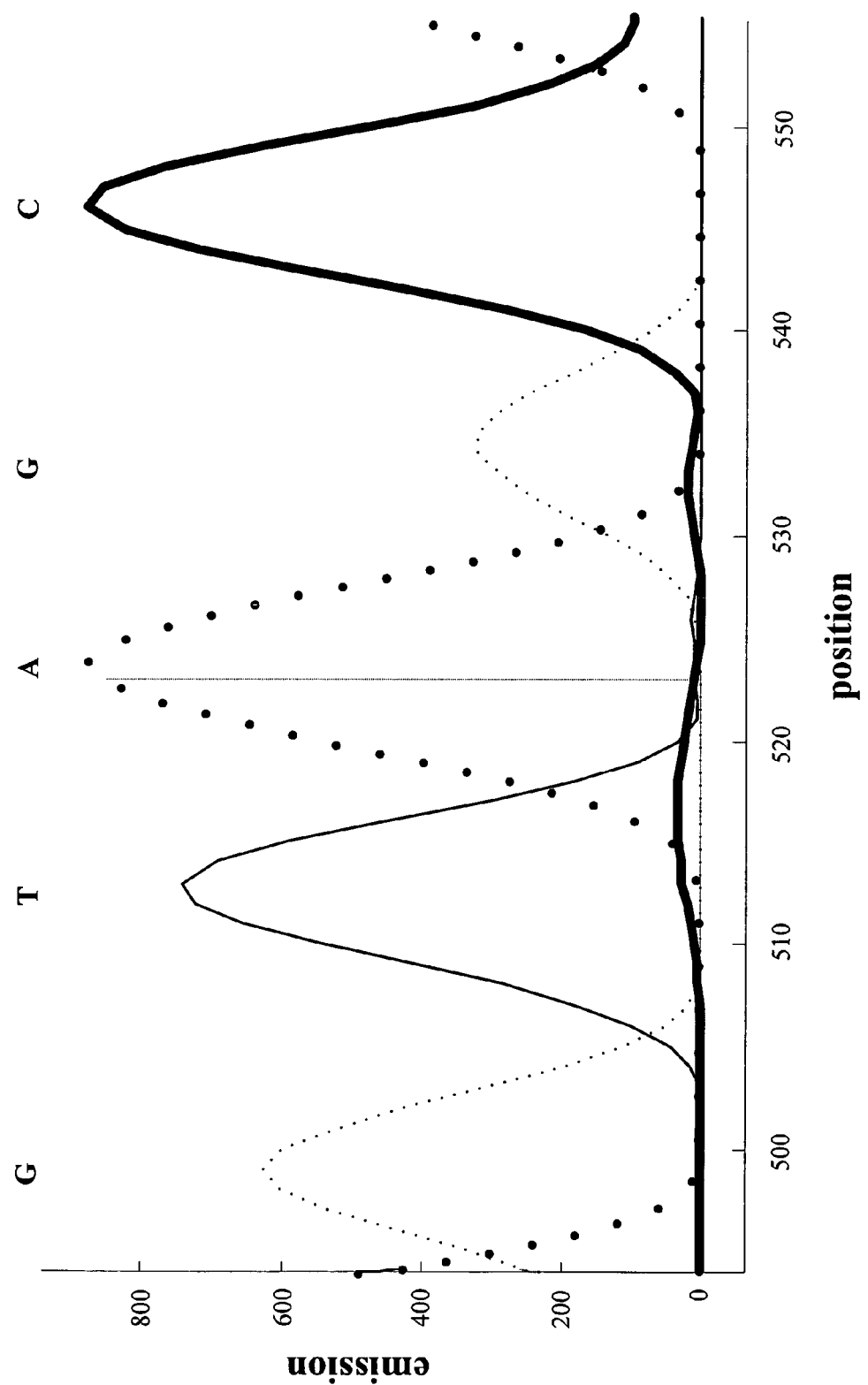
FIG. 1 schematically illustrates a chromatogram.
Figure 2:
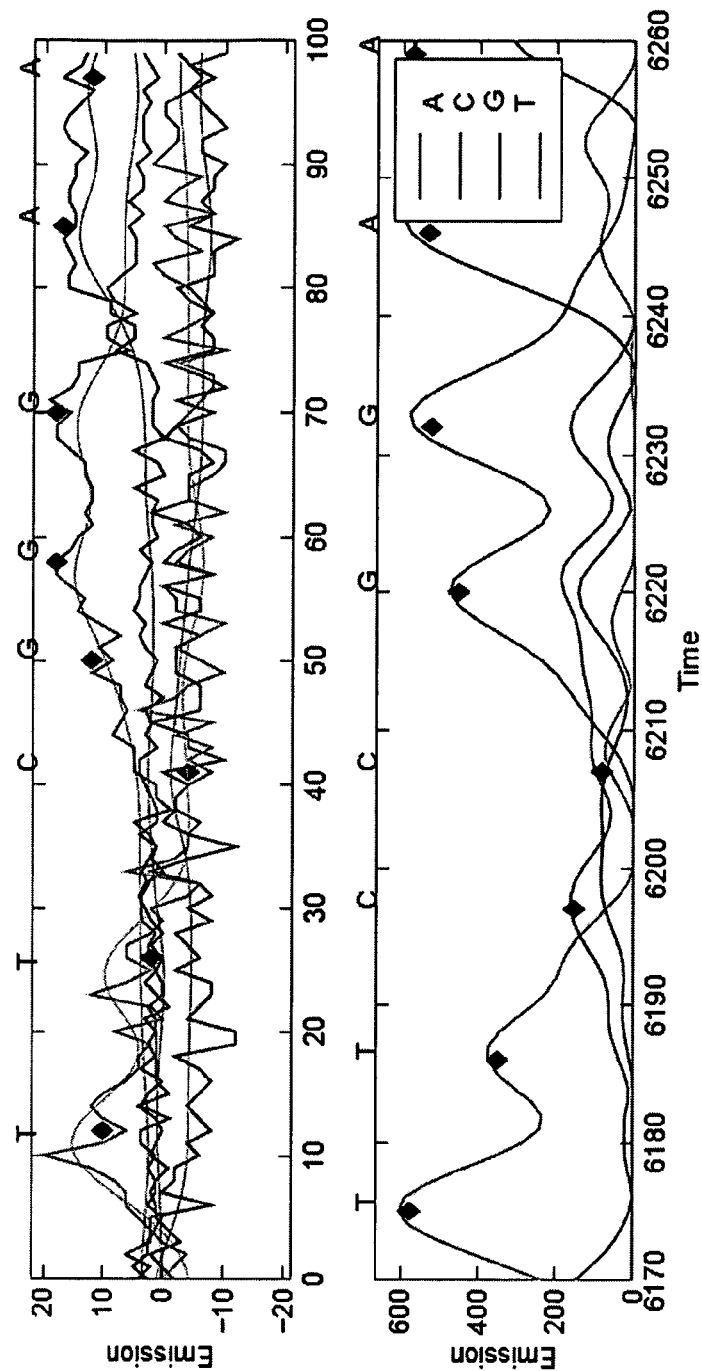
FIG. 2 provides an example of raw data and processed data.
Figure 3:
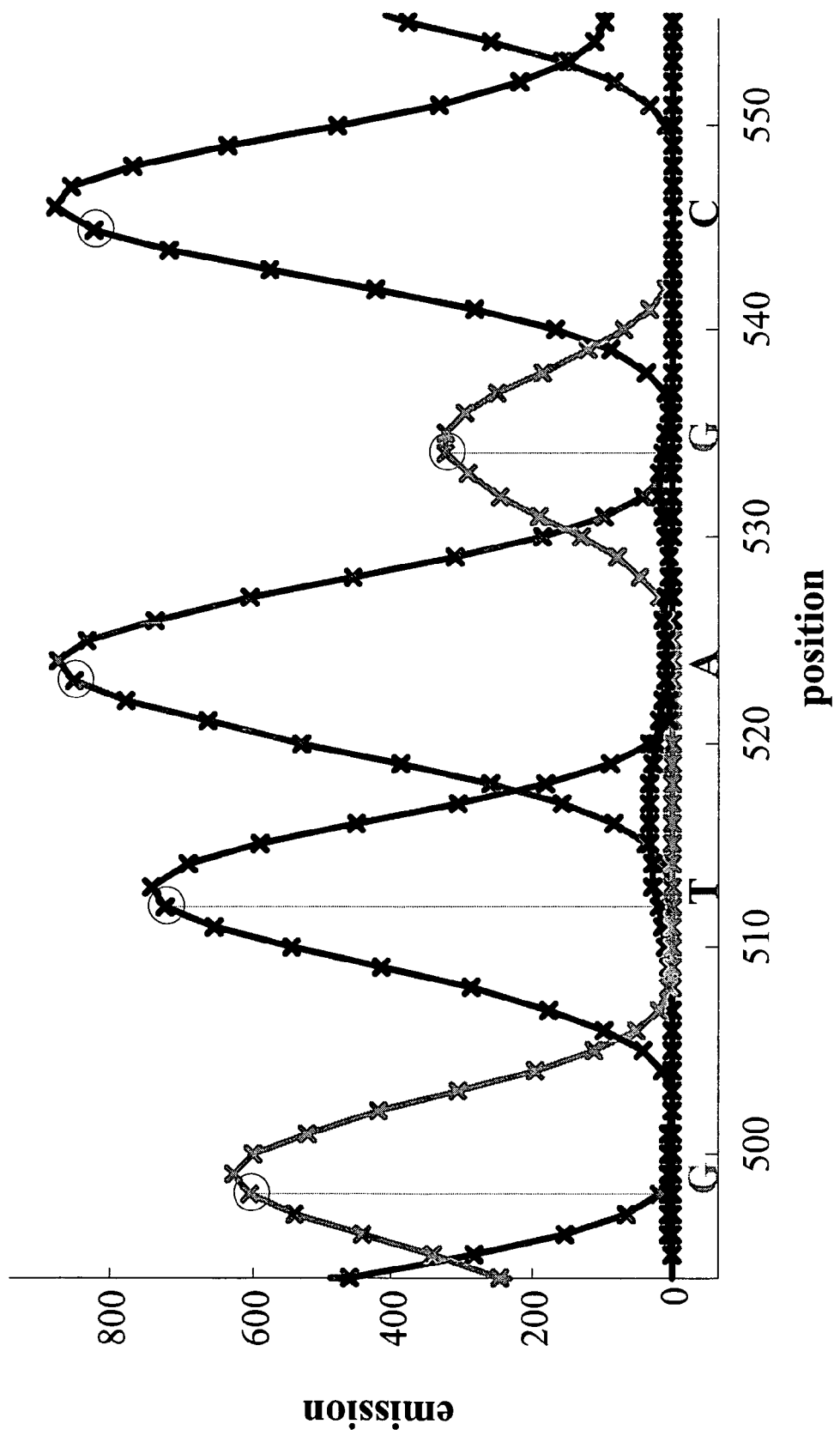
FIG. 3 schematically illustrates the sampled data points that determine the peaks of a chromatogram.

The term "sequence" generally refers to a molecular sequence, for instance, a nucleotide sequence (e.g., DNA, RNA). The term "sequencing" generally refers to a process for identifying the components of a molecular sequence. For example, DNA can be amplified and sequenced using PCR, the Sanger chain termination method and an automated DNA sequencer as described above. RNA can be sequenced by first converting the RNA to a complementary DNA strand (cDNA) using the reverse transcriptase polymerase chain reaction (RT-PCR) followed by sequencing the cDNA. The RNA sequence is complementary to the sequenced cDNA with the exception that the RNA strands have uracil at those cDNA positions having a thymine. Since RNA viruses, such as HIV, use reverse transcriptase (RT) in vivo to reverse transcribe the viral RNA to viral cDNA (which is then incorporated into the host's genome), those portions of the host's genome corresponding to the viral DNA can be sequenced directly.

The term "sample" generally refers to one or more molecular entities to be analyzed. Samples can be singular sequences or polymorphic mixtures of sequences. Polymorphic samples can be, for example, DNA corresponding to strains of a highly-mutable virus or to variable and highly variable regions of a genome or any other sample of mixed sequences (e.g., DNA complementary to a mixed RNA sample). The samples can be naturally occurring or synthetic molecular entities.

Mixed samples can arise because DNA replication during cell division is imperfect and this can result in mutations being introduced into the genome. Mutations can be a single nucleotide change (point or site mutation) or insertions/deletions (indels) of subsequences. HIV is very prone to site mutations and indels, which make chromatography difficult because, as described above, the algorithm utilized by existing base callers is based on the assumption that the sequencer will produce clean data (i.e., one peak per sequence position). When a sample containing mixtures of DNA from different viral strains is analyzed, many positions have more than one peak (corresponding to differences in the sequences) and this can result in inaccurate base calls.

The subject matter described herein relates to a hierarchical statistical framework for separating mixed data. The approach is a shift from chaining hard-decision modules to an integrated soft-decision approach. By way of example, machine learning (e.g., statistical inference, EM, VEM, etc.) can be used to decipher mixed sequence data (e.g., chromatograms) obtained from a polymorphic genetic sample.

As described above, a base caller assigns a peak to a sequence position by determining the sample of the data with the largest amplitude (the peak) in a given distribution. However, because the base caller makes its decisions on data obtained at a low sampling rate, this can result in the base caller relying on a data point that is not a true peak when calling the base. To address this issue, the emissions data can be preprocessed to improve the base calls. By way of example, Gaussian peaks can be fitted to the data. By way of another example, template peak shape can be learned from the raw traces.

In the latter case, the chromatogram signals can be represented as a sum of a small number of such templates, scaled and shifted to fit the data, according, for instance, to the following equation:

$$y(x) = \sum_k a_k s(x - x_k) + \text{noise}$$

where $x_k$ and $a_k$ represent the position and the amplitude of the peak, and the function $s(x)$ representing the template shape. If the noise is Gaussian, this can also be written as:

$$y(x) \sim N\left(\sum_k a_k s(x - x_k), d^2\right)$$

where ~ is the notation for "distributed as," N(m,f) represents a Gaussian distribution with mean m and variance f, y(x) refers to any or all of the four traces in a chromatogram, or multiple chromatograms, which are all expected to consists of trains of template shapes s(x). The positions $x_k$, amplitudes $a_k$, and the shape s(x) (discretely sampled across values of x, or parameterized as a continuous function, such as a bell function or Gaussian with various parameters, for example, width) can all now be fitted iteratively so as to maximize the likelihood of the observation (or multiple observations) of chromatogram traces y(x).

One efficient implementation of this iterative procedure starts with a guess for function s(x), for example, an extracted single peak shape from the data, and employs a search over positions $x_k$ where adding a shape $s(x-x_k)$ maximally reduces the error of the signal approximation. For each position, $a_k$ that best fits the signal is estimated by setting the derivative of the Gaussian likelihood to zero and solving for $a_k$. Once the signal y(x) has been fitted in the maximum likelihood sense, the best peak shape s(x) can now be re-estimated by maximizing the likelihood with respect to parameters of s(x), which, as mentioned, either can be parameters of a continuous function or simply a set of values of s(x) for each discrete value of x in a region where the shape template s(x) is expected to be larger than zero (typically around 20-30 samples). Both parameterizations have been successfully tested. This iterative procedure can be further iterated with other steps of maximizing the likelihood of the fitted amplitudes and positions of peaks. More generally, the parameterization of the raw signal can be added to the rest of the model described below to compute a single likelihood function for all the data, leading to a joint inference and parameter optimization for all model components.

To accurately call the bases of a chromatogram representing different sequence groups (e.g., strains, alleles, etc.), the correspondence between the viral strain and the peaks must be determined. Machine learning techniques, such as statistical inference, can be used to determine this correspondence. Statistical inferences (e.g., Bayesian, frequentist, etc.) are made by parametrically modeling a distribution of data and estimating the parameters from the observed data. To model the data, certain statistical assumptions (constraints) about the data are made. In the case of chromatograms representing mixtures of nucleic acid sequences, the constraints can relate to the number of sequences present in the mixed sample, the positions of the peaks corresponding to a particular sequence and the content of the sequences. The peaks of the chromatogram are determined and assigned to a sequence group (e.g., strain, allele, etc.) according to the constraints.

The constraints can include, for instance, that the number of different sequences in the sample is proportional to the ambiguities (e.g., multiple peaks clustered together) present in the data. For instance, it can be assumed that a sequence with many two-way ambiguities but none that are three-way represents a mixture of two sequences. Similarly, a sequence with many three-way ambiguities but none that are four-way represents a mixture of three sequences. The number of strains in the chromatogram also can be estimated by Bayesian model selection, where multiple models, each postulating a different number of strains, are fitted to the data with appropriate prior on each level of complexity. The posterior distribution over models then is computed to provide a level of belief for each postulated number of mixed strains. Other exemplary constraints include that the peak amplitude is proportional to DNA fragment concentration and that peak position is proportional to DNA fragment mass. Additional constraints can include, for example, that peaks from the same sequence are equally spaced and that peaks from different sequences are shifted in phase by a constant amount from each other.

One way to represent the correspondence between different sequences in a mixture and the peaks of a chromatogram is by a mapping (as schematically illustrated in FIG. 4). It is convenient to express the mapping in matrix format 510, 520 as shown in FIG. 5A. The rows of the binary matrix $R^k$ represent base positions j and the columns represent the peaks i. If element $r_{ij}^k=1$, this indicates that peak i in the chromatogram is mapped to base position j in the sequence k. A transformation matrix 510 ($R^k$) can be multiplied by the complete set of peak base positions X 550 to yield the set of base positions of peaks corresponding to that strain 560 ($H^k$) as shown in FIG. 5B. As indicated by the garbage can icon 410 and by all zeros in the $7^{th}$ column 530, 540 of both of the matrices 510, 520 (corresponding to the $7^{th}$ peak 420), one or more peaks can be deemed due to noise and discarded.

The constraints can be expressed mathematically as parametric functions and machine learning techniques can be used to estimate the parameters (e.g., expectation maximization (EM), variational expectation maximization (VEM), Bayes estimation, maximum likelihood estimation, etc.). For instance, the peak-spacing constraints discussed above can be written in terms of probability distributions for the peaks positions as:

$$h_{j;j>1}^1 \sim N(h_{j-1}^1 + \Delta_1, \sigma_1^2)$$
$$h_j^{k;k>1} \sim N(h_j^1 + \Delta_k, \sigma_k^2)$$

where j is the base position, $h^1$ is the base position of the first peak, N is a Gaussian distribution, $\Delta$ is the spacing between two peaks and $\sigma^2$ is the variance of the peak spacing. As explained above, the base positions h in chromatograms correspond to the peaks $x_i$ of the template shapes in the chromatogram. The peak amplitude can be modeled as a normal distribution centered on sequence-group specific means as follows:

$$a_i | R \sim N(\Sigma_k R_{ji} \mu_k, \Sigma_k R_{ji} \phi_k^2)$$

where a is the amplitude of a sample of the emissions data, R is the transformation matrix, $\mu$ is the mean of the amplitudes and $\phi^2$ is the variance of the amplitudes.

Information known about the content of the nucleotide sequence under study can be incorporated into the model to account for site mutations/indels. For instance, the alignment of the bases of the sequences of the mixed data can be measured relative to a known sequence or diversity profile. One way to accomplish this is by using a profile parameter $T^k$ that points to a position in a diversity profile serving as a prior on the sequence content according to the following constraint:

$$L^k | R \sim \tilde{O}_{k,j} w_{T_k+j}(\ell_j^k)$$

where w is the diversity profile, T is an offset relative to the diversity profile, and l is the letter of the nucleotides of the sequences under study. By way of example, the diversity profile can be based on a consensus sequence or the diversity profile can be learned from some or all known sequences of the type under study.

The joint distribution of the likelihood functions can be written as follows:

$$P(L,A,X,R,H)=P(R) \cdot P(H) \cdot P(X|R,H) \cdot P(A|R) \cdot P(L|R)$$

Figure 6A:
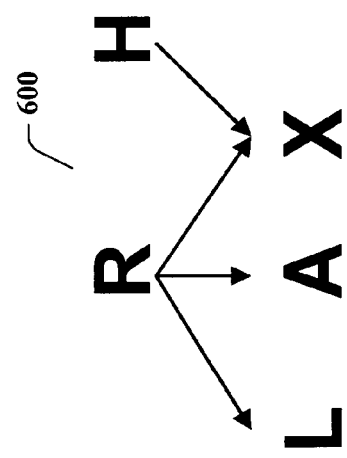
FIG. 6A is an exemplary Bayes net structure pertaining to an exemplary joint distribution.
Figure 6B:
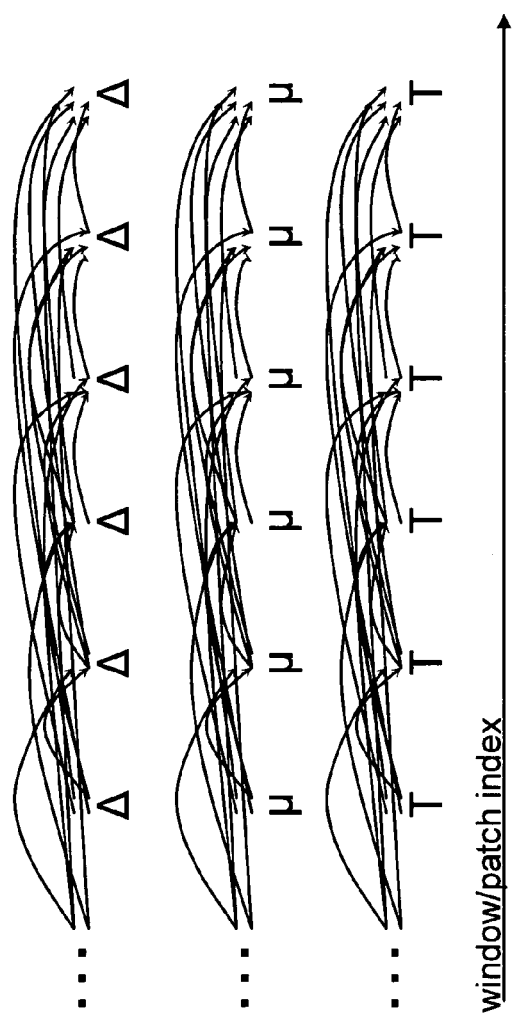
FIG. 6B schematically illustrates estimating parameters using overlapping windows of sequencing data.

This is represented in FIG. 6A as a Bayes net structure 600. The model is repeated for overlapping sliding windows (patches) of data from the chromatogram to allow for evolution of the phase ($\Delta,\sigma^2$), amplitude ($\mu,\phi^2$) and profile (T) parameters. Using overlapping windows of data allows for data from the cumulative previous patches to serve as a prior on the current patch as shown schematically in FIG. 6B. Thus, parameters will be slightly different between overlapping windows.

Amplitude and phase parameters are initialized to uninformative (e.g., $\mu_k=1$ for strains $k\neq 1$, and $\mu_0=0$ for the garbage component). An efficient search over matrices $R^k$ then is successively performed for each window to optimize the likelihood given the propagated phase and amplitude parameters. These parameters are propagated down the chain only in one direction, as the decoding is done in a single pass. The size of the trace window can be chosen such that it contains at least 9 peaks in each strain, but other sizes can be used. To integrate decoded sequences in different windows, we determine the global peak mapping N×J matrices $\{R^1, \ldots R^K\}$ by summing each column of $R^k$ over all windows that include the peak, weighting terms by their likelihoods. If the strains cross over (strain #1 becomes #2 and vice versa) from one window to the next (which most often occurs in areas of serious insertion/deletion disruption), this can be automatically detected by breaks in the steady incrementing of the profile index pointers. Such situations can be addressed by testing for strain reversal to increase the likelihood over several windows.

The term "system" is intended to refer to a computer-related entity, either hardware, software and/or firmware. For example, a system can be a process running on a processor, a processor, an object, an executable, a program, and/or a computer. By way of illustration, both an application running on a server and the server can be a system. One or more systems can reside within a process and a system can be localized on one computer and/or distributed between two or more computers.

The term "component" is intended to refer to a computer-related entity, either hardware, a combination of hardware and software, software, or software in execution. For example, a component can be, but is not limited to a process running on a processor, a processor, an object, an executable file, a thread of execution, a program, and a computer. By way of illustration, an application running on a server and/or the server can be a component. In addition, a component can include one or more subcomponents. One or more components can reside within a process and/or thread of execution and a component can be localized on one computer and/or distributed between two or more computers. A thread is the entity within a process that the operating system kernel schedules for execution. Each thread can have an associated context, which is the volatile data associated with the execution of the thread. A thread's context includes the contents of system registers and the virtual address belonging to the thread's process. Thus, the actual data comprising a thread's context varies as it executes.

Figure 7:
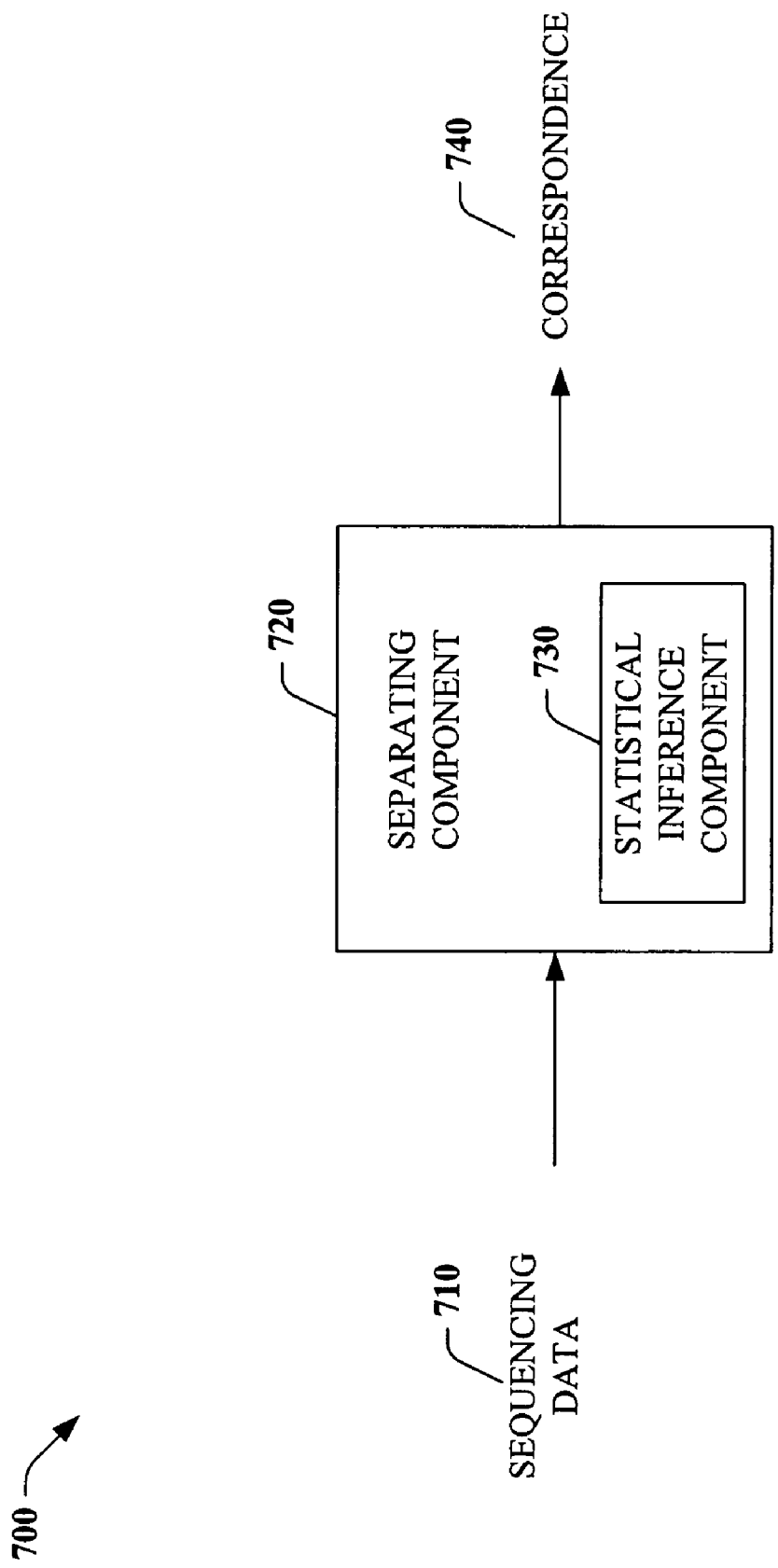
FIG. 7 illustrates an exemplary system that facilitates separating sequencing data.

FIG. 7 shows an exemplary system 700 that facilitates separating sequencing data 710. The system 700 has a separating component 720 to separate the sequencing data 710 obtained from a mixed sample, for instance a mixture of two or more nucleic acids having different sequences. The separating component 720 can use a statistical inference component 730 to infer the correspondence 740 between the sequencing data 710 and the two or more nucleic acids to separate the sequencing data 710.

The sequencing data 710 can be, for instance, a chromatogram or any other data relating to the sequences of the two or more nucleic acids. The sequencing data 710 can reside locally relative to the separating component 720 or be sent to the separating component 720 from a remote device (not shown). The mixed sample can contain, for instance, a population of differently mutated viral strains, polymorphic genetic material or any other multi-sequence mixture of molecular entities. One example of a mixed sample of DNA is a sample of viral DNA obtained from a patient infected with a rapidly-evolving pathogen such as HIV.

The statistical inference component 730 can utilize one or a combination of machine learning techniques (e.g., expectation maximization (EM), variational expectation maximization (VEM), variational decoupling, iterative learning, temporal smoothing, clever indexing, Bayesian inference, etc.) to infer the correspondence 740 between the sequencing data and the two or more nucleic acids. The statistical inference component 730 can infer the correspondence 740, for example, by utilizing overlapping windows of the sequencing data 710. The correspondence 740 can be expressed, for example, as a mapping such as a transformation matrix. The expression of the correspondence 740 is not limited to a matrix, and can be expressed in any suitable form for expressing an association between the mixed data and the nucleic acids.

Figure 8:
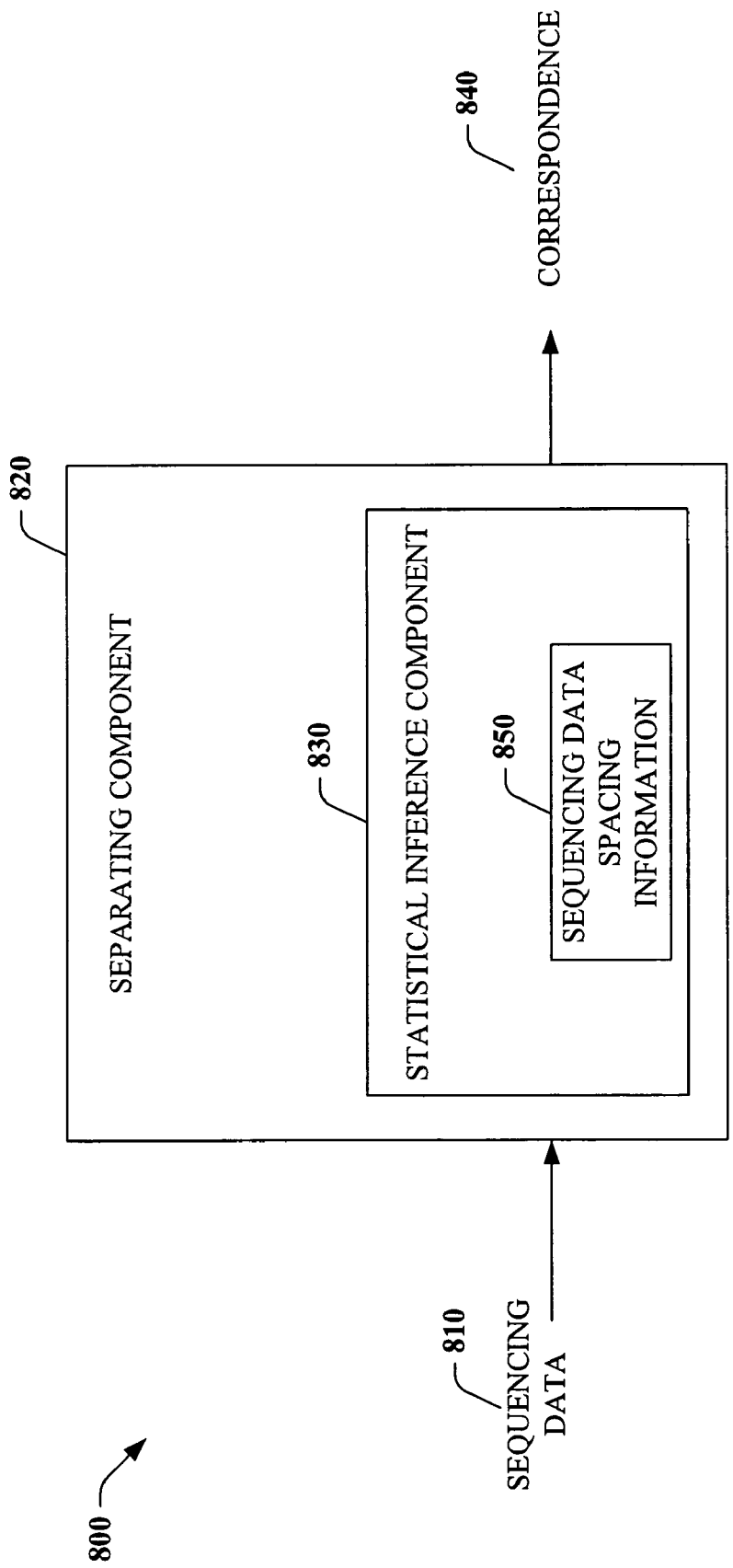
FIG. 8 illustrates another exemplary system that facilitates separating sequencing data.

FIG. 8 shows another exemplary system 800 that facilitates separating sequencing data 810. The system 800 has a separating component 820 to separate the sequencing data 810 obtained from a mixed sample, for instance a mixture of two or more nucleic acids having different sequences. The separating component 820 can use a statistical inference component 830 to infer the correspondence 840 between the sequencing data 810 and the two or more nucleic acids to separate the sequencing data 810.

The statistical inference component 830 infers the correspondence 840 based at least in part on sequencing data spacing information 850. The sequencing data spacing information 850 can be, for example, any suitable information relating to the spacing of the sequencing data, such as the distance between the peak values, the phase shift of the peak values and the covariance of the peak values.

Figure 9:
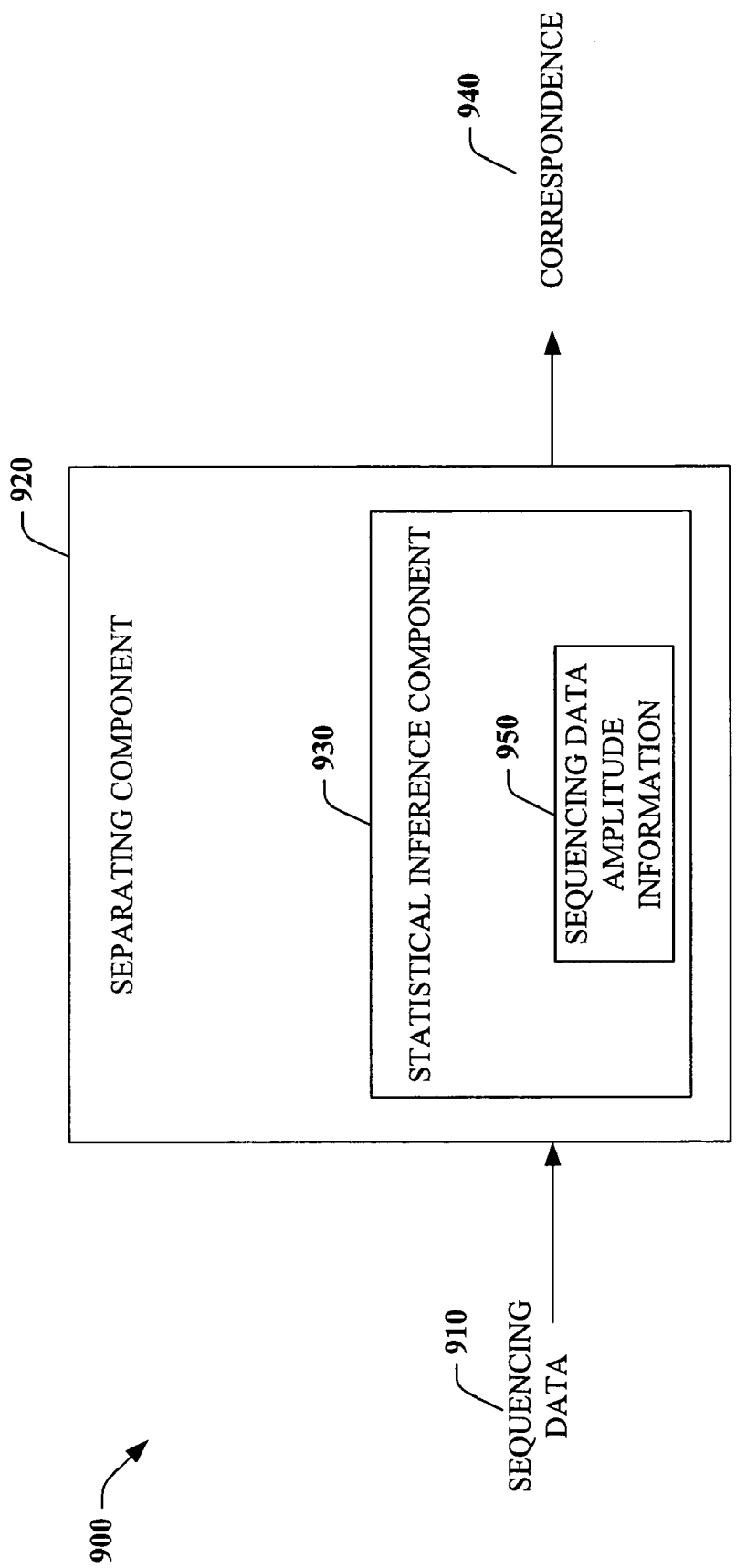
FIG. 9 illustrates another exemplary system that facilitates separating sequencing data.

FIG. 9 shows another exemplary system 900 that facilitates separating sequencing data 910. The system 900 has a separating component 920 to separate sequencing data 910 obtained from a mixed sample, for instance a mixture of two or more nucleic acids having different sequences. The separating component 920 can use a statistical inference component 930 to infer the correspondence 940 between the sequencing data 910 and the two or more nucleic acids to separate the sequencing data 910.

The statistical inference component 930 infers the correspondence 940 based at least in part on sequencing data amplitude information 950. The sequencing data amplitude information 950 can be, for example, any suitable information relating to the amplitude of the sequencing data 910, such as the mean of the amplitude values and the covariance of the amplitude values.

Figure 10:
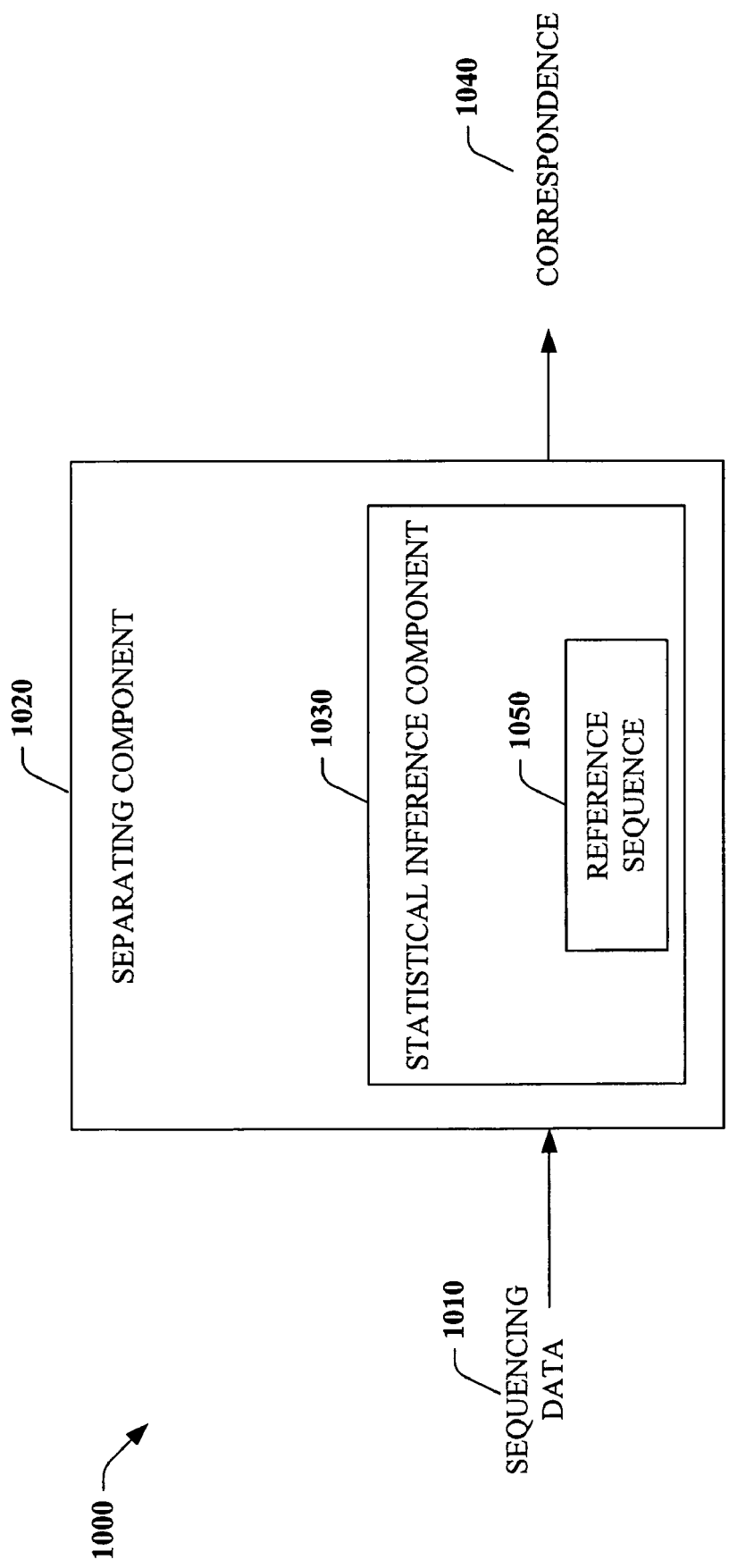
FIG. 10 illustrates another exemplary system that facilitates separating sequencing data.

FIG. 10 shows another exemplary system 1000 that facilitates separating sequencing data 1010. The system 1000 has a separating component 1020 to separate the sequencing data 1010 obtained from a mixed sample, for instance a mixture of two or more nucleic acids having different sequences. The separating component 1020 can use a statistical inference component 1030 to infer the correspondence 1040 between the sequencing data 1010 and the two or more nucleic acids to separate the sequencing data 1000.

The statistical inference component 1030 infers the correspondence 1040 based at least in part on a reference sequence 1050 of the same type as the two or more nucleic acids having different sequences. The reference sequence 1050 can be, for example, any suitable known sequence of the same type, such as a consensus sequence, a diversity profile and combinations of two or more known sequences of the same type. Moreover, the reference sequence 1050 can be machine-learned from known sequences of the same type as the two or more nucleic acids.

Figure 11:
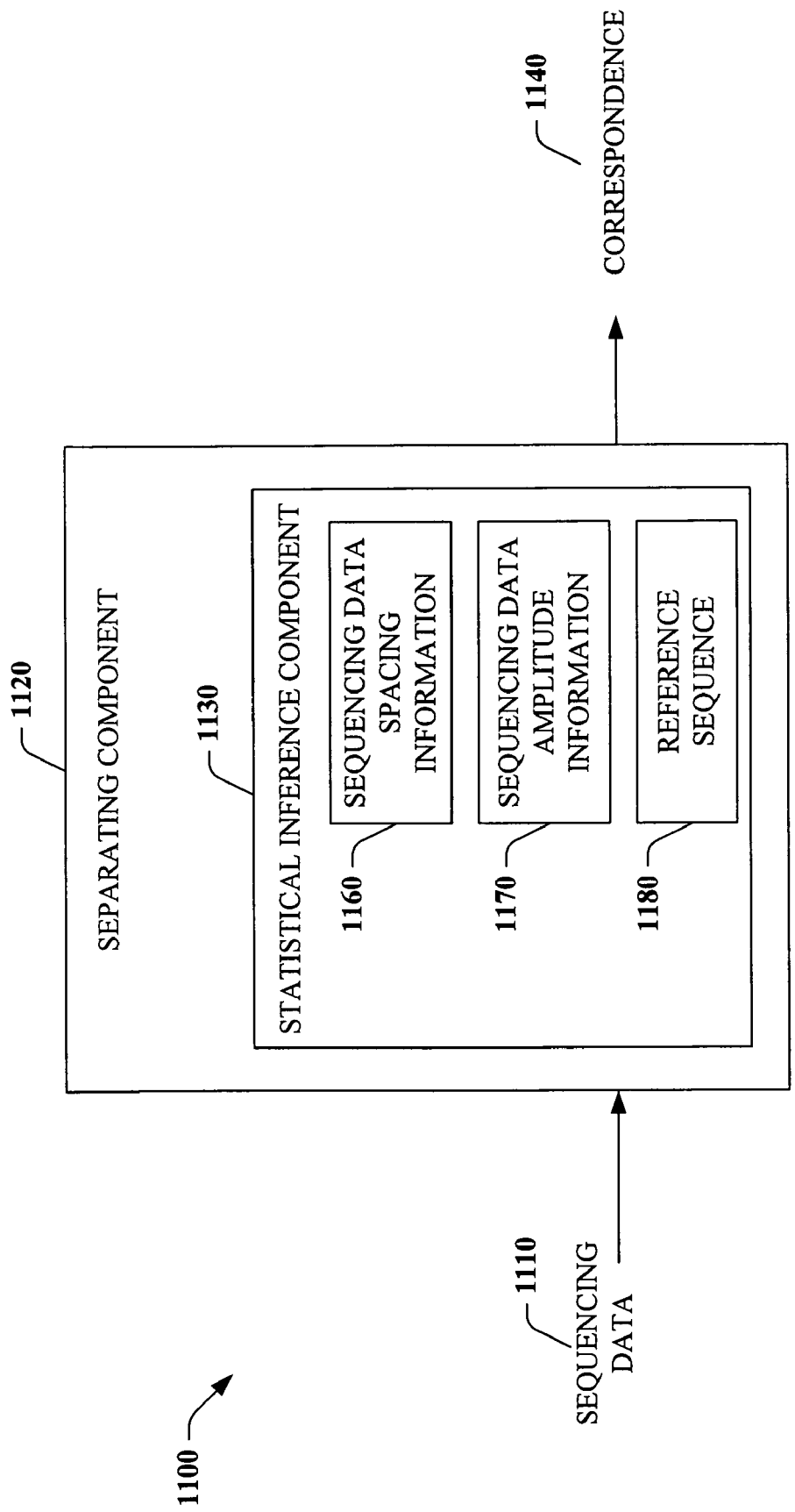
FIG. 11 illustrates yet another exemplary system that facilitates separating sequencing data.

FIG. 11 shows another exemplary system 1100 that facilitates separating sequencing data 1110. The system 1100 has a separating component 1120 to separate the sequencing data 1110 obtained from a mixed sample, for instance a mixture of two or more nucleic acids having different sequences. The separating component 1120 can use a statistical inference component 1130 to infer the correspondence 1140 between the sequencing data 1110 and the two or more nucleic acids to separate the sequencing data 1110. The statistical inference component 1130 infers the correspondence 1140 based at least in part on sequencing data spacing information 1160, sequencing data amplitude information 1170 and a reference sequence 1180 of the same type as the two or more nucleic acids having different sequences.

Figure 12:
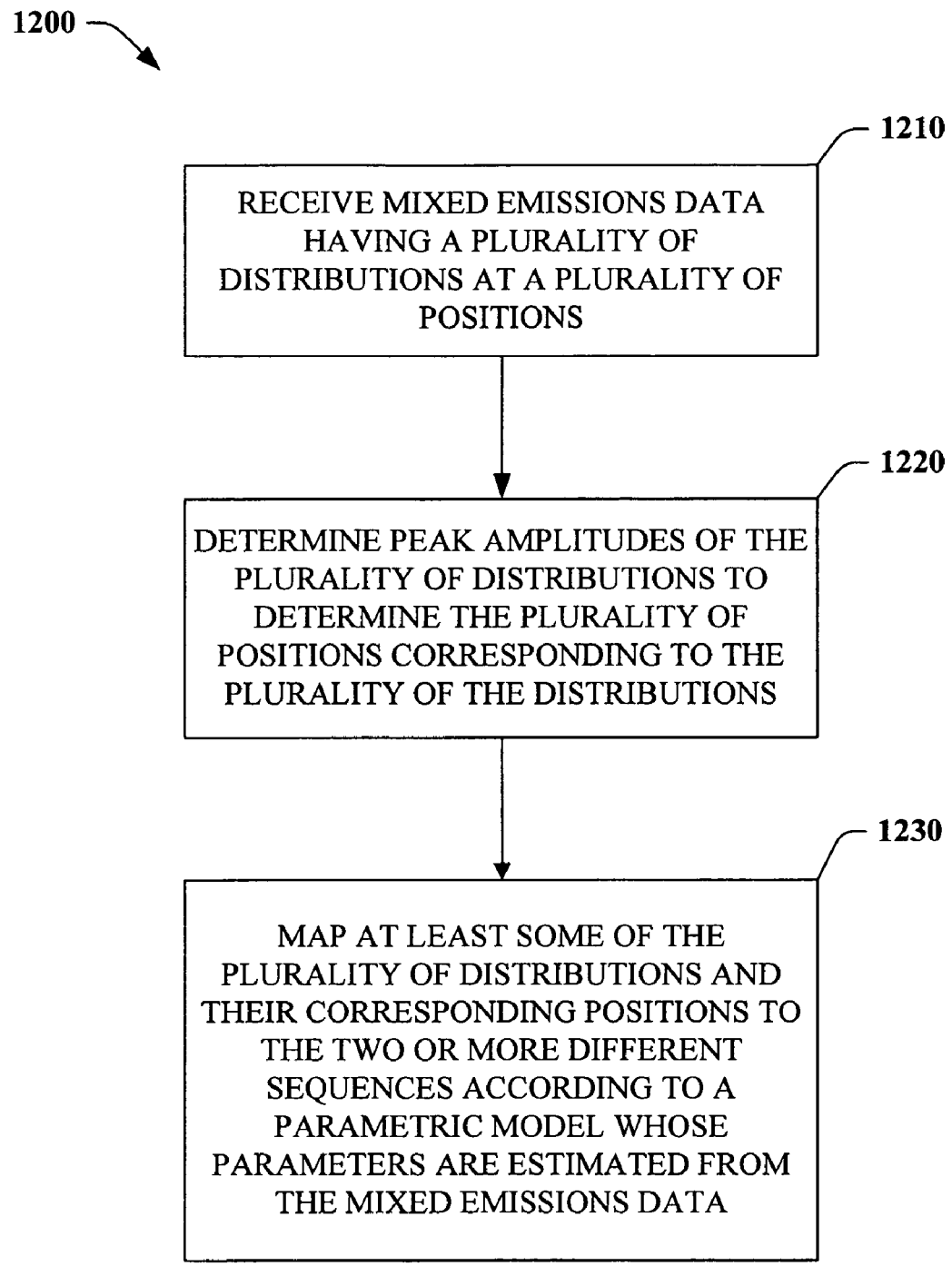
FIG. 12 illustrates a method of sequencing two or more different sequences.

FIG. 12 is a flowchart detailing a method 1200 of sequencing two or more different sequences. At step 1210, mixed emissions data having a plurality of distributions at a plurality of positions and obtained from the two or more different sequences is received. The mixed emissions data can be received, for instance, by retrieval from a local storage device and/or retrieved from a remote source over a network. The mixed emissions data can be, for example, fluorescent emissions from an automated nucleotide sequencer. The mixed emissions data can be raw data or preprocessed data.

At step 1220, the peak amplitude of the plurality of distributions is determined in order to determine the positions corresponding to the plurality of distributions. By way of example, the mixed emissions data can be preprocessed to determine the positions corresponding to the plurality of distributions by fitting Gaussian peaks to the emissions data or by learning template peak shapes and fitting learned template shapes to the mixed emissions data.

At step 1230, at least some of the plurality of distributions and their corresponding positions are mapped to the two or more different sequences according to a parametric model whose parameters are estimated from the mixed emissions data. The parameters can be estimated from the mixed emissions data, for instance, by utilizing overlapping windows of data. The mapping can be, for example, a transformation matrix or any other mapping expressing an association between the mixed emissions data and the plurality of distributions.

By way of example, the parameters of the parametric model can model phase, amplitude and nucleotide information. The parametric model can model the phase and amplitude according to constraints such as the distributions are equally-spaced, distributions mapping to a sequence other than the first sequence occur at a constant phase-shift from distributions of the first sequence and amplitudes are normally distributed around sequence-specific means. By way of another example, the parametric model can constrain the nucleotide information according to a diversity profile, such as a machine-inferred diversity profile.

As used in this application, the term "means" is intended to refer to a computer-related entity, either hardware, a combination of hardware and software, software, or software in execution. For example, a means can be, but is not limited to being, a process running on a processor, a processor, an object, an executable, a thread of execution, a program, and/or a computer. By way of illustration, both an application running on a server and the server can be a means. One or more means can reside within a process and/or thread of execution and a means can be localized on one computer and/or distributed between two or more computers.

Figure 13:
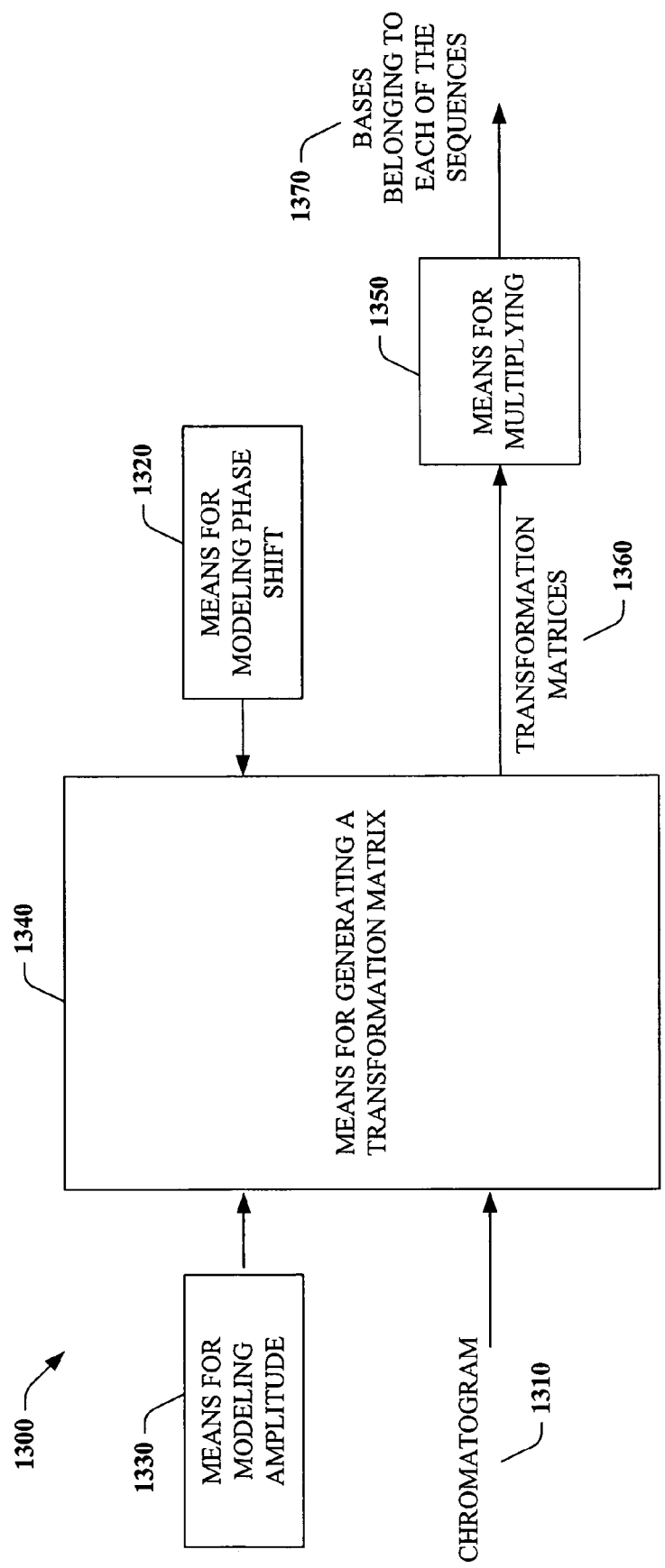
FIG. 13 illustrates a system for base calling a mixture of different sequences represented as a chromatogram.

FIG. 13 shows a system 1300 for base calling a mixture of different sequences represented in a chromatogram 1310. The system 1300 includes a means for modeling phase shift 1320 of the plurality of peaks of the chromatogram 1310, a means for modeling amplitude 1330 of the plurality of peaks of the chromatogram 1310, a means for generating a transformation matrix 1340 for each of the different sequences and a means for multiplying 1350 the transformation matrices 1360 by a set of base positions to determine the bases belonging to each of the different sequences. The means for generating a transformation matrix 1340 utilizes the means for modeling phase shift 1320 and the means for modeling amplitude 1330 to determine the transformation matrices 1360 by analyzing overlapping windows of the chromatogram.

The means for modeling phase shift 1320 can be, for example, computer-executable instructions encoding an algorithm for estimating the parameters of a parametric function that models chromatogram peak-spacing. The means for modeling amplitude 1330 can be, for example, computer-executable instructions encoding an algorithm for estimating the parameters of a parametric function that models chromatogram amplitude. The means for generating a transformation matrix 1340 can be, for example, computer-executable instructions for inferring transformation matrices 1360 from chromatogram data. Any suitable machine-learning technique or combinations of techniques can be used to estimate the parameters and infer transformation matrices 1360 (e.g., expectation maximization (EM), variational expectation maximization (VEM), Bayes estimation, maximum likelihood estimation, variational decoupling, clever indexing, temporal smoothing, iterative learning, etc.).

Figure 14:
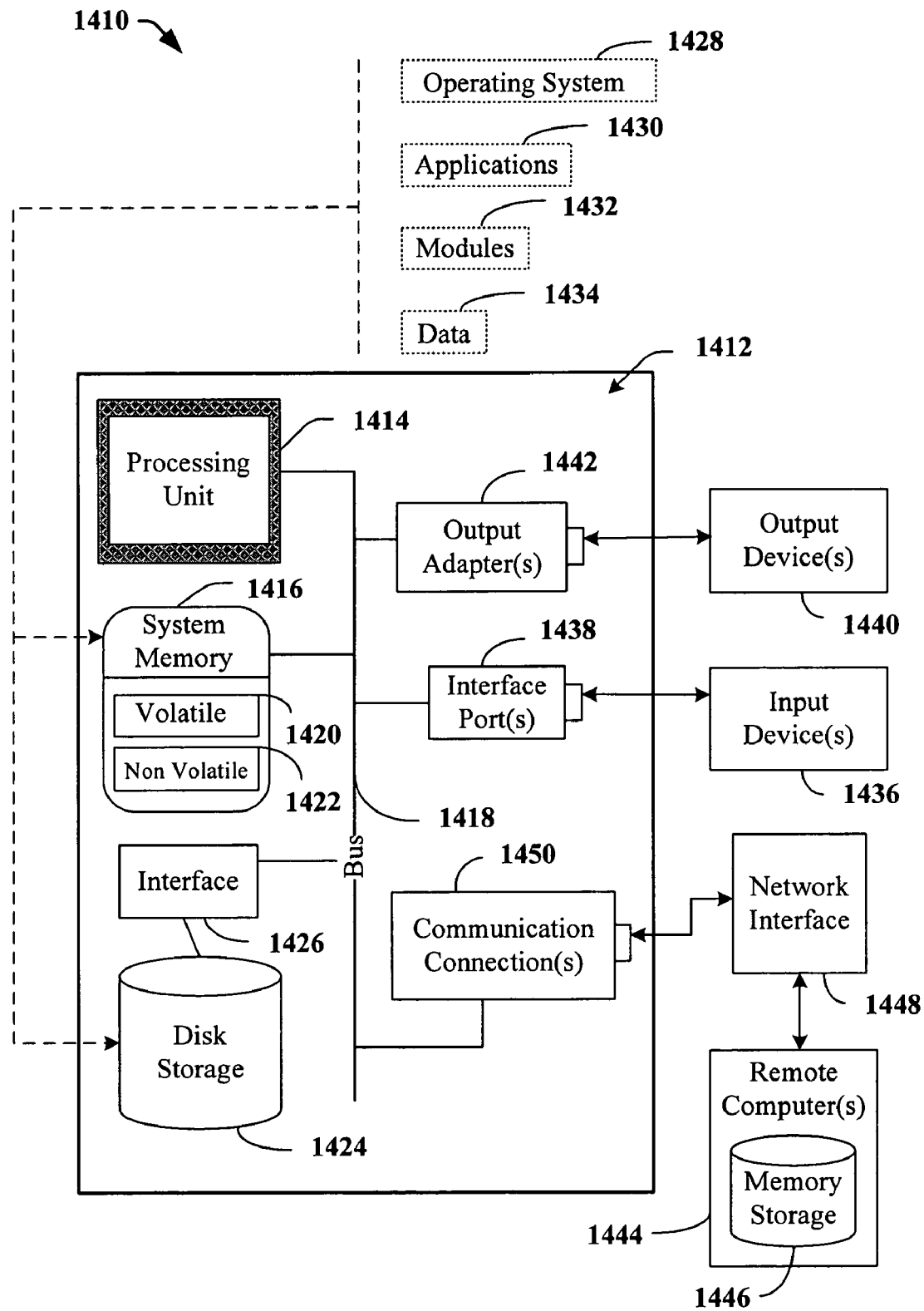
FIG. 14 illustrates an exemplary computing architecture.
Figure 15:
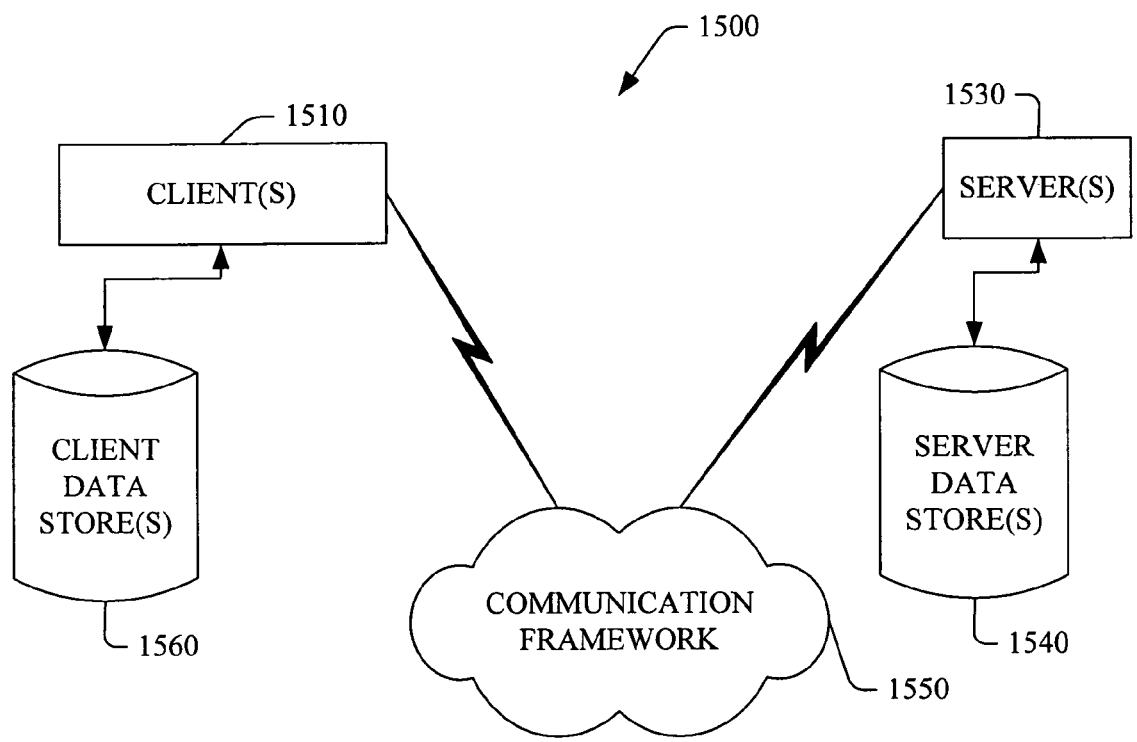
FIG. 15 illustrates an exemplary networking environment.

FIGS. 14-15 and the following discussion are intended to provide a brief, general description of a suitable computing environment in which the various aspects of the subject matter can be implemented. While the subject matter has been described above in the general context of computer-executable instructions of a computer program that runs on a local computer and/or remote computer, the subject matter also can be implemented in combination with other program modules.

Moreover, the subject matter can be practiced with other computer system configurations, including single-processor or multi-processor computer systems, minicomputers, mainframe computers, as well as personal computers, hand-held computing devices, microprocessor-based and/or programmable consumer electronics and the like, each of which may operatively communicate with one or more associated devices. The subject matter also can be practiced in distributed computing environments such that certain tasks are performed by remote processing devices that are linked through a communications network. In a distributed computing environment, program modules may be located in local and/or remote memory storage devices. However, some, if not all, of the subject matter can be practiced on stand-alone computers.

The subject matter can operate in the general context of computer-executable instructions, such as program modules, executed by one or more components. Generally, program modules include routines, programs, objects, data structures, etc., that perform particular tasks or implement particular abstract data types. Typically, the functionality of the program modules may be combined or distributed as desired.

FIG. 14 schematically illustrates an exemplary environment 1410 for implementing various aspects of the subject matter. The environment 1410 includes a computer 1412, which includes a processing unit 1414, a system memory

1416 and a system bus 1418. The system bus 1418 couples system components including, but not limited to, the system memory 1416 to the processing unit 1414. The processing unit 1414 can be any of various available processors. Dual microprocessors and other multiprocessor architectures also can be employed as the processing unit 1414.

The system bus 1418 can be any of several types of bus structure(s) including the memory bus or memory controller, a peripheral bus or external bus, and/or a local bus using any variety of available bus architectures including, but not limited to, 10-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Universal Serial Bus (USB), Advanced Graphics Port (AGP), Personal Computer Memory Card International Association bus (PCM-CIA), and Small Computer Systems Interface (SCSI).

The system memory 1416 includes volatile memory 1420 and nonvolatile memory 1422. The basic input/output system (BIOS) containing the basic routines to transfer information between elements within the computer 1412, such as during start-up, is stored in nonvolatile memory 1422. By way of illustration, and not limitation, nonvolatile memory 1422 can include read only memory (ROM), programmable ROM (PROM), electrically programmable ROM (EPROM), electrically erasable programmable ROM (EEPROM), or flash memory. Volatile memory 1420 includes random access memory (RAM), which can act as an external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and Rambus Direct RAM (RDRAM), direct Rambus dynamic RAM (DRDRAM), and Rambus dynamic RAM (RDRAM).

Computer 1412 also includes removable/non-removable, volatile/non-volatile computer storage media. FIG. 14 illustrates, for example a disk storage device 1424. Disk storage device 1424 includes, but is not limited to, devices like a magnetic disk drive, floppy disk drive, tape drive, Jaz drive, Zip drive, LS-100 drive, flash memory card, or memory stick. In addition, disk storage device 1424 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1424 to the system bus 1418, a removable or non-removable interface is typically used such as interface 1426.

In addition to hardware components, FIG. 14 illustrates software that acts as an intermediary between users and the basic computer resources described in suitable operating environment 1410. Such software includes an operating system 1428. Operating system 1428, which can be stored on disk storage devices 1424, acts to control and allocate resources of the computer system 1412. System applications 1430 take advantage of the management of resources by operating system 1428 through program modules 1432 and program data 1434 stored either in system memory 1416 or on disk storage devices 1424. The subject matter can be implemented with various operating systems or combinations of operating systems.

A user enters commands or information into the computer 1412 through input device(s) 1436. Input devices 1436 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1414 through the system bus 1418 via interface port(s) 1438. Interface port(s) 1438 include, for example, a serial port, a parallel port, a game port, and a universal serial bus (USB). Output device(s) 1440 use some of the same type of ports as input device(s) 1436. Thus, for example, a USB port may be used to provide input to computer 1412 and to output information from computer 1412 to an output device 1440. Output adapter 1442 is provided to illustrate that there are some output devices 1440 like monitors, speakers, and printers, among other output devices 1440, which require special adapters. The output adapters 1442 include, by way of illustration and not limitation, video and sound cards that provide a means of connection between the output device 1440 and the system bus 1418. It should be noted that other devices and/or systems of devices provide both input and output capabilities such as remote computer(s) 1444.

Computer 1412 can operate in a networked environment using logical connections to one or more remote computers, such as remote computer(s) 1444. The remote computer(s) 1444 can be a personal computer, a server, a router, a network PC, a workstation, a microprocessor based appliance, a peer device or other common network node and the like, and typically includes many or all of the elements described relative to computer 1412. For purposes of brevity, only a memory storage device 1446 is illustrated with remote computer(s) 1444. Remote computer(s) 1444 is logically connected to computer 1412 through a network interface 1448 and then physically connected via communication connection 1450. Network interface 1448 encompasses communication networks such as local-area networks (LAN) and wide-area networks (WAN). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1450 refers to the hardware/software employed to connect the network interface 1448 to the bus 1418. While communication connection 1450 is shown for illustrative clarity inside computer 1412, it can also be external to computer 1412. The hardware/software necessary for connection to the network interface 1448 includes, for exemplary purposes only, internal and external technologies such as, modems including regular telephone grade modems, cable modems and DSL modems, ISDN adapters, and Ethernet cards.

FIG. 15 is a schematic block diagram of a sample-computing environment 1500 with which the subject matter can interact. The system 1500 includes one or more client(s) 1510. The client(s) 1510 can be hardware and/or software (e.g., threads, processes, computing devices). The system 1500 also includes one or more server(s) 1530. The server(s) 1530 also can be hardware and/or software (e.g., threads, processes, computing devices). The servers 1530 can house threads to perform transformations by employing the subject matter.

One possible communication between a client 1510 and a server 1530 can be in the form of a data packet or signal manufactured to be transmitted between two or more computer processes. The system 1500 includes a communication framework 1550 that can be employed to facilitate communications between the client(s) 1510 and the server(s) 1530.

The client(s) 1510 can connect to one or more client data store(s) 1560 that can be employed to store information local to the client(s) 1510. Similarly, the server(s) 1530 can connect to one or more server data store(s) 1540 that can be employed to store information local to the servers 1530.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It is, of course, not possible to describe every conceivable combination of components or methodologies that fall within the claimed subject matter, and many further combinations and permutations of the subject matter are possible. While a particular feature may have been disclosed with respect to only one of several implementations, such feature may be combined with one or more other features of the other implementations of the subject matter as may be desired and advantageous for any given or particular application.

In regard to the various functions performed by the above described components, computer-executable instructions, means, systems and the like, the terms are intended to correspond, unless otherwise indicated, to any functional equivalents even though the functional equivalents are not structurally equivalent to the disclosed structures. Furthermore, to the extent that the terms "includes," and "including" and variants thereof are used in either the specification or the claims, these terms are intended to be inclusive in a manner similar to the term "comprising." Accordingly, the claimed subject matter is intended to embrace all such alterations, modifications, and variations that fall within the spirit and scope of the appended claims.

What is claimed is:

1. Computer storage media comprising instructions encoding a method of sequencing two or more different sequences, the method comprising:
   receiving mixed emissions data obtained from the two or more different sequences, the mixed emissions data having a plurality of distributions at a plurality of positions;
   determining peak amplitudes of the plurality of distributions to determine the plurality of positions corresponding to the plurality of distributions; and
   mapping at least some of the plurality of distributions and the corresponding positions of at least some of the plurality of distributions to the two or more different sequences according to a parametric model having parameters that are estimated utilizing overlapping, sliding windows of data from the mixed emissions data where cumulative data from previous windows of data serve as a prior for a current window of data, the mapping to sequence the two or more different sequences, the estimated parameters being used to model phase, amplitude and nucleotide information.

2. The computer storage media of claim 1, wherein determining peak amplitudes of the plurality of distributions to determine the plurality of positions corresponding to the plurality of distributions comprises preprocessing the mixed emissions data by fitting Gaussian peaks to the plurality of distributions.

3. The computer storage media of claim 1, wherein determining peak amplitudes of the plurality of distributions to determine the plurality of positions corresponding to the plurality of distributions comprises preprocessing the mixed emissions data by machine learning template peak shapes and fitting the machine learned template peak shapes to the plurality of distributions.

4. The computer storage media of claim 1, wherein the parametric model models phase, amplitude and sequence content.

5. The computer storage media of claim 4, wherein phase is modeled according to a constraint comprising distributions that are equally-spaced.

6. The computer storage media of claim 5, the constraint further comprising distributions mapping to a sequence other than a first sequence which occur at a constant phase-shift from distributions of the first sequence.

7. The computer storage media of claim 4, wherein amplitude is modeled according to a constraint comprising amplitudes that are normally distributed around sequence-specific means.

8. The computer storage media of claim 4, wherein content of the two or more sequences is modeled using statistical assumptions and a diversity profile, wherein the diversity profile is learned from known sequences.

9. The computer storage media of claim 8, wherein the diversity profile is machine-inferred.

10. The computer storage media of claim 1, wherein mapping according to a parametric model having parameters that are estimated from the mixed emissions data comprises generating a transformation matrix.

11. The computer storage media of claim 1, wherein the parameters are estimated from overlapping windows of the mixed emissions data.

12. A system comprising:
   means for receiving mixed emissions data obtained from the two or more different sequences, the mixed emissions data having a plurality of distributions at a plurality of positions;
   means for determining peak amplitudes of the plurality of distributions to determine the plurality of positions corresponding to the plurality of distributions; and
   means for mapping at least some of the plurality of distributions and the corresponding positions of at least some of the plurality of distributions to the two or more different sequences according to a parametric model having parameters that are estimated utilizing overlapping, sliding windows of data from the mixed emissions data where cumulative data from previous windows of data serve as a prior for a current window of data, the mapping to sequence the two or more different sequences, the estimated parameters being used to model phase, amplitude and nucleotide information.

13. A method implemented at least in part on a computing device, the method comprising:
   receiving mixed emissions data obtained from the two or more different sequences, the mixed emissions data having a plurality of distributions at a plurality of positions;
   determining, by a processor of the computing device, peak amplitudes of the plurality of distributions to determine the plurality of positions corresponding to the plurality of distributions; and
   mapping at least some of the plurality of distributions and the corresponding positions of at least some of the plurality of distributions to the two or more different sequences according to a parametric model having parameters that are estimated utilizing overlapping, sliding windows of data from the mixed emissions data where cumulative data from previous windows of data serve as a prior for a current window of data, the mapping to sequence the two or more different sequences, the estimated parameters being used to model phase, amplitude and nucleotide information.

14. The method of claim 13, wherein determining peak amplitudes of the plurality of distributions to determine the plurality of positions corresponding to the plurality of distributions comprises preprocessing the mixed emissions data by machine learning template peak shapes and fitting the machine learned template peak shapes to the plurality of distributions.

15. The method of claim 13, wherein the parametric model models phase, amplitude and sequence content.

16. The method of claim 15, wherein phase is modeled according to a constraint comprising distributions that are equally-spaced.

17. The method of claim 16, the constraint further comprising distributions mapping to a sequence other than a first sequence which occur at a constant phase-shift from distributions of the first sequence.

18. The method of claim 15, wherein amplitude is modeled according to a constraint comprising amplitudes that are normally distributed around sequence-specific means.

19. The method of claim 15, wherein content of the two or more sequences is modeled using statistical assumptions and a machine-inferred diversity profile, wherein the diversity profile is learned from known sequences.

20. The method of claim 13, wherein mapping according to a parametric model having parameters that are estimated from the mixed emissions data comprises generating a transformation matrix.

* * * * *